(12) United States Patent
Springer et al.

(10) Patent No.: US 6,852,755 B1
(45) Date of Patent: Feb. 8, 2005

(54) NITROGEN MUSTARD COMPOUNDS AND PRODRUGS THEREFOR

(75) Inventors: Caroline J. Springer, Surrey (GB); Lawrence C. Davies, Surrey (GB)

(73) Assignee: Cancer Research Campaign Technology Limited, London (GB)

( * ) Notice: Subject to any disclaimer, the term of this patent is extended or adjusted under 35 U.S.C. 154(b) by 0 days.

(21) Appl. No.: 09/937,714

(22) PCT Filed: Mar. 29, 2000

(86) PCT No.: PCT/GB00/01194
§ 371 (c)(1),
(2), (4) Date: Oct. 1, 2001

(87) PCT Pub. No.: WO00/58271
PCT Pub. Date: Oct. 5, 2000

(30) Foreign Application Priority Data

Mar. 31, 1999 (GB) .............................................. 9907414

(51) Int. Cl.$^7$ .................... A61K 31/235; A61K 31/255; C07C 229/14; C07C 303/00; C07C 313/00
(52) U.S. Cl. ........................ 514/517; 514/533; 558/47; 558/48; 562/565; 562/126
(58) Field of Search ................................ 514/533, 517, 514/483, 490; 558/47, 48; 562/565, 126; 560/133, 21, 24, 25

(56) References Cited

FOREIGN PATENT DOCUMENTS

EP          A 415 731       3/1991

(List continued on next page.)

OTHER PUBLICATIONS

Jen et al, 1965, Huaxue Xuebao, 31(6), p. 486–92, 500.*

(List continued on next page.)

Primary Examiner—Cecilia J. Tsang
Assistant Examiner—Taylor V Oh
(74) Attorney, Agent, or Firm—Nixon & Vanderhye P.C.

(57) ABSTRACT

This invention pertains to nitrogen mustard compounds (Formula (II)) and prodrugs therefor (Formula (I)), methods for their preparation, pharmaceutical compositions comprising such compounds, and the use of such compounds and compositions, both in vitro and in vivo, in therapy and treatment, for example, of cancer, wherein: $R^1$ and $R^2$ are independently —Cl, —Br, —I, —OSO$_2$CH$_3$, or —OSO$_2$Ph; $R^{1a}$, $R^{2a}$, $R^{1b}$, and $R^{2b}$ are independently —H, a C$_{1-4}$alkyl group, or a C$_{1-4}$haloalkyl group; $R^3$ is —F, —Cl, —Br, —I, —OCHF$_2$, —C≡CH, —OCF$_3$, —CH$_3$, —CF$_3$, —SF$_5$, —SCF$_3$, or —CF$_2$CF$_3$; $R^4$ is —H or as defined for $R^{3-}$, $R^5$ is —H or —F; $R^7$ is —H, —C(CH$_3$)$_3$, or —CH$_2$—CH=CH$_2$; Z is —CH$_2$—T—W; T is —CH$_2$—, —O—, —S—, —(S=O)—, or —(SO$_2$)—; W is one of: (1) —COOH; (2)—(C=O)OR$^8$; (3) —(C=O)NR$^9$R$^9$; (4) —SO$_2$NHR$^{10-}$, (5) SO$_2$OR$^{11}$; (6)—PO$_3$R$^{11}$R$^{11}$; (7) a tetrazol-5-yl group; (8) —CONH—SO$_2$R$^{12}$; and, (9)-M-Het.

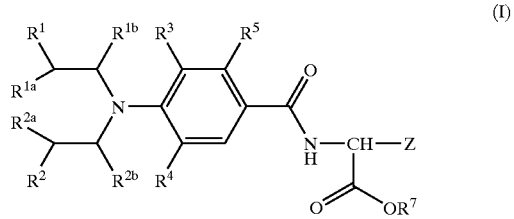

(I)

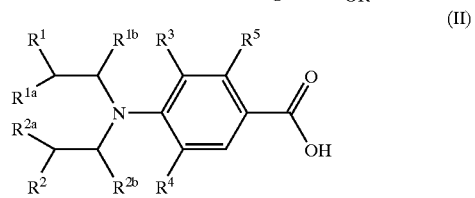

(II)

52 Claims, 1 Drawing Sheet

FOREIGN PATENT DOCUMENTS

| WO | WO 88/07378 | 10/1988 |
| --- | --- | --- |
| WO | WO 90/02729 | 3/1990 |
| WO | WO 91/02805 | 3/1991 |
| WO | WO 91/03460 | 3/1991 |
| WO | WO 92/14829 | 9/1992 |
| WO | WO 93/10814 | 6/1993 |
| WO | WO 94/02450 | 2/1994 |
| WO | WO 94/21792 | 9/1994 |
| WO | WO 94/25429 | 11/1994 |
| WO | WO 95/07994 | 3/1995 |
| WO | WO 95/14091 | 5/1995 |
| WO | WO 96/03151 | 2/1996 |
| WO | WO 96/03515 | 2/1996 |
| WO | WO 96/22277 | 7/1996 |
| WO | WO 97/03957 | 2/1997 |
| WO | WO 97/26918 | 7/1997 |

OTHER PUBLICATIONS

Davis et al, 1950, J. of Chemical Soc., p. 1331–1337.*

Karpavicius et al, 1979, Izvestiya Akademii Nauk SSSSR, 1, p. 51–58.*

Karpavicius et al, 1977, Poiski Izuch. p. 66–75.*

Ivanova et al, 1975, Leikozoologiya, 4, p. 23–29.*

Prasmickiene et al, 1969, Izvestiya Akademii nauk SSSSR, 3, p. 643–646.*

Bagshawe et al., "Antibody–Enzyme Conjugates Can Generate Cytotoxic Drugs from Inactive Precursors at Tumor Sites" *Antibody, Immunoconjugates, and Radiopharmaceuticals*, 1991, vol. 4, pp. 915–922.

Cornell and Charm. "Purification of Carboxypeptidase G–1 by Immunoadsorption" *Biotech. and Bioeng.*, 1976. vol. XVIII. 1171–1173.

Culver et al., "In Vivo Gene Transfer with Retroviral Vector–Producer Cells for Treatment of Experimental Brain Tumors" *Science*. 1992. vol. 256. pp. 1550–1552.

Englehardt et al., "Direct gene transfer of human CFTR into human bronchial epithelia of xenografts with E1–deleted adenoviruses" *Nature Genetics*, 1993. vol. 4. pp. 27–34.

Huber et al. "Retroviral–mediated gene therapy for the treatment of hepatocellular carcinoma: An innovative approach for cancer therapy" *Proc. Natl. Acad. Sci. USA*. 1991. vol. 88. pp. 8039–8043.

Levy and Goldman, "The Enzymatic Hydrolysis of Methotrexate and Folic Acid" *J. Biol. Chem.*, 1967. vol. 12, 2933–2938.

Mizushima and Nagata. "pEF–BOS. a powerful mammalian expression vector" *Nucl. Acids Res.*, 1990, vol. 18. p. 5322.

Niculescu–Duvaz et al., "Prodrugs for Antibody– and Gene––Directed Enzyme Prodrug Therapies (ADEPT and GDEPT)." *Anti–Cancer Drug Design*. 1999. vol. 14. pp. 517–538.

Springer et al., Optimization of Alkylating Agent Prodrugs Derived from Phenol and Aniline Mustards: A New Clinical Candidate Prodrug (ZD2767) for Antibody–Directed Enzyme Prodrug Therapy (ADEPT). *J. Med. Chem.*, 1995. vol. 38. pp. 5051–5065.

Springer et al., "Comparison of half–lives and cytotoxicity of N–chloroethyl–4–amino and N–mesyloxyethyl–benzoyl compounds, products of prodrugs in antibody–directed enzyme prodrug therapy (ADEPT)" *Anti–Cancer Drug Design*, 1991. vol. 6. pp. 467–479.

Springer et al., "Novel Prodrugs Which Are Activated to Cytotoxic Alkylating Agents by Carboxypeptidase G2" *J. Medicinal Chem.*, 1990. vol. 33. pp. 677–681.

Yasuda et al. "In Vitro Antitumor Activity of Carboxypeptidase $G_3$ from *Pseudomonas* sp. M–27" *Bull. Mukogawa. Women's Univ. Nat. Sci.* 1994, vol. 42. pp. 63–66.

* cited by examiner

NITROGEN MUSTARD COMPOUNDS AND PRODRUGS THEREFOR

The present application is a 371 U.S. National Phase of PCT/GB00/1194, filed Mar. 29, 2000.

TECHNICAL FIELD

This invention pertains to nitrogen mustard compounds (Formula II) and prodrugs therefor (Formula I), methods for their preparation, pharmaceutical compositions comprising such compounds, and the use of such compounds and compositions, both in vitro and in vivo, in therapy and treatment, for example, of cancer.

BACKGROUND

Over the years, many cytotoxic compounds have been discovered which are of potential use in cancer chemotherapy. Nitrogen mustards from one important family of such cytotoxic compounds. Nitrogen mustards are nitrogen analogs of mustard gas, $S(CH_2CH_2Cl)_2$. The clinical use of cytotoxic compounds in general, and nitrogen mustards in particular, has been limited because of the poor selectivity in the cytotoxic effect between tumour cells and normal cells.

One approach to overcome this problem has involved the development of so-called prodrugs which are derivatives of the cytotoxic drug, often relatively simple derivatives, whose cytotoxic properties are considerably reduced compared to those of the parent drugs. Numerous proposals have been made for the administration of such prodrugs to patients under regimes whereby the prodrug is only converted to the cytotoxic drug in the region of the intended site of action, for example, by the action of an enzyme.

A variety of systems exist for delivery of the enzyme. One such system is described in WO 88/07378, and involves conjugating the enzyme to an antibody specific for a tumour marker, delivering the antibody enzyme conjugate to a patient, allowing the conjugate to localise, and then delivering the prodrug to the patient. This system is referred to as "antibody-directed enzyme prodrug therapy" (ADEPT).

Various other proposals for delivery of the enzyme to the desired site of action exist, including "gene-directed enzyme prodrug therapy" (GDEPT), in which a vector such as a viral vector carrying a gene encoding the prodrug-converting enzyme is delivered to cells at the desired site of action (Huber et al, Proc. Natl. Acad. Sci. USA, (1991) Vol. 88, p. 8039). GDEPT is also described in WO 96/03151.

A further alternative system, often referred to as "ligand-directed enzyme prodrug therapy" (LIDEPT), is to provide a ligand, generally a naturally occurring polypeptide whose biological role involves its binding to a cognate receptor on the surface of the cell, conjugated to the prodrug-activating enzyme. Such a system is described in WO 97/26918, where VEGF is particularly exemplified as an example of a ligand.

One class of prodrugs suggested for use in the above systems is that of prodrugs of nitrogen mustard compounds. Benzoic acid nitrogen mustards, such as the one shown below, are bifunctional alkylating agents, and a variety of prodrugs of such compounds are described in the art.

One class of such prodrugs comprise a protecting group which may be removed by the action of a carboxypeptidase enzyme, such as bacterial carboxypeptidase G, including such enzymes available from Pseudomans species, such as carboxypeptidase G2 (CPG2). In many cases, the carboxylic acid group, —COOH, of the drug is protected as an amide, —CONHR, in the prodrug, for example, by reaction with an α-amino acid (e.g., glutamic acid) or a polypeptide chain, R—$NH_2$. The prodrug is converted into the active drug by cleavage of the amide bond, —CONH—, between the residue of the α-amino acid or oligopeptide and the residue of the benzoic acid nitrogen mustard. This enzyme, and prodrugs which may be activated by it have been described in various publications. WO 88/07378 pertains to certain nitrogen mustard compounds of the following formula, where X and Y are —Cl and —$OSO_2CH_3$, or both —$OSO_2CH_3$, or both —$OSO_2CF_3$, and R is the residue of an α-amino acid $RNH_2$, for example, glutamic acid.

Springer et al., J. Medicinal Chem., (1990) Vol. 33, pp. 677–681 and Springer et al., Anti-Cancer Drug Design (1991), Vol. 6, pp. 467–479 pertain to certain nitrogen mustard compounds of the following formula, wherein X and Y are —Cl or —$OSO_2CH_3$.

WO 94/02450 pertains to certain nitrogen mustard compounds of the following formula, wherein X is —O—, —NH—, or —$CH_2$— and Y is =O.

WO 94/25429 pertains to certain 2-fluoro- and 3-fluoro-substituted nitrogen mustard compounds of the following formula, wherein the group —NH—R is the residue of an α-amino acid $NH_2$—R or oligopeptide $NH_2$—R, and Y and

L, which may be the same or different in a given molecule, are leaving groups:

WO 96/03515 pertains to GDEPT systems which employ certain nitrogen mustard compounds of the following formula of the formulae shown below, in which X is —C(=O)—, —OC(=O)—, -NHC(=O)—, or —CH$_2$—C(—O)— and Z$_1$ is —O— or —NH—.

WO 96/22277 pertains to certain nitrogen mustard compounds of the following Formula, in which Z$^1$ is —O— or —NH—.

Thus although a number of nitrogen mustard prodrugs exist in the art, there is a continuing need for improved prodrugs, which can provide enhanced efficacy, for example by having an improved ratio of toxicity between prodrug and active drug form, better half-life or more potency.

SUMMARY OF THE INVENTION

One aspect of the present invention pertains to prodrug compounds of the Formula I:

and drug compounds of the Formula II:

as described herein.

In one preferred embodiment, $R^1$ and $R^2$ are independently —I, —Br, or —Cl.

In one preferred embodiment, $R^1$ and $R^2$ are both —I.

In one preferred embodiment, $R^{1a}$, $R^{1b}$, $R^{2a}$, $R^{2b}$ are each independently —H or —CH$_3$.

In one preferred embodiment, $R^{1a}$, $R^{1b}$, $R^{2a}$, $R^{2b}$ are all —H.

In one preferred embodiment, $R^3$ and $R^4$ are —CF$_3$ and —H, respectively.

In one preferred embodiment, $R^3$ and $R^4$ are both —F.

In one preferred embodiment, $R^3$ and $R^4$ are —CF$_3$ and —H, respectively; and, $R^5$ is —H.

In one preferred embodiment, $R^3$ and $R^4$ are both —F; and, $R^5$ is —F.

In one preferred embodiment, $R^3$ and $R^4$ are both —F; and, $R^5$ is —H.

In one preferred embodiment, Z is —CH$_2$—T—C(=O)OH or —CH$_2$—T—C(=O)OR$^8$; and, T is —CH$_2$—.

In one preferred embodiment, $R^8$ is —H, —C(CH$^3$)$_3$, or —CH, —CH=CH$_2$.

In one preferred embodiment, the compound is selected from:
{3,5-difluoro-4-[bis(2-iodoethyl)amino]benzoyl}-L-glutamic acid;
{3,5-difluoro-4-[bis (2-chloroethyl) amino]benzoyl}-L-glutamic acid;
{3,5-difluoro-4-[bis (2-bromoethyl) amino]benzoyl}-L-glutamic acid;
{2,3,5-trifluoro-4-[bis(2-chloroethyl)amino]benzoyl}-L-glutamic acid;
{2,3,5-trifluoro-4-[bis(2-bromoethyl)amino]benzoyl}-L-glutamic acid;
{2,3,5-trifluoro-4-[bis(2-iodoethyl)amino]benzoyl}-L-glutamic acid;
{3,5-difluoro-4-[bis (2-bromopropyl) amino]benzoyl}-L-glutamic acid;
{3-trifluoromethyl-4-[bis(2-bromoethyl)amino]benzoyl}-L-glutamic acid; and,
the di-tert-butyl esters thereof.

In one preferred embodiment, the compound is selected from:
3,5-difluoro-4-[bis(2-iodoethyl)amino]benzoic acid;
3,5-difluoro-4-[bis(2-chloroethyl)amino]benzoic acid;
3,5-difluoro-4-[bis(2-bromoethyl)amino]benzoic acid;
2,3,5-trifluoro-4-[bis(2-chloroethyl)amino)benzoic acid;
2,3,5-trifluoro-4-[bis(2-bromoethyl)amino]benzoic acid;
2,3,5-trifluoro-4-[bis(2-iodoethyl)amino]benzoic acid;
3,5-difluoro-4-[bis(2-bromopropyl)amino]benzoic acid; and
3-trifluoromethyl-4-lbis(2-bromoethyl)amino]benzoic acid.

Another aspect of the present invention pertains to two-component systems comprising:
(i) a first component capable of delivering a carboxypeptidase enzyme to the interior or exterior of a target cell or a vector encoding said enzyme to the interior of said cell such that said vector expresses said enzyme in said cell, and (ii) a prodrug as described herein capable of being converted by said enzyme into a drug as described herein.

Another aspect of the present invention pertains to kits comprising:
(a) a prodrug compound as described herein; and,
(b) one of:
  (i) an immunoglobulin/enzyme fusion protein or conjugate in which the immunoglobulin is specific for a cellular antigen and the enzyme is a carboxypeptidase enzyme;
  (ii) a ligand/enzyme conjugate or fusion protein, the ligand being specific for a cellular antigen and the enzyme is a carboxypeptidase enzyme;
    (iii) a vector which encodes a carboxypeptidase enzyme which can be expressed in a cell.

Another aspect of the present invention pertains to a composition comprising a drug or prodrug compound as described herein, and a pharmaceutically acceptable carrier or diluent.

Another aspect of the present invention pertains to a drug or prodrug compound as described herein for use in a method of treatment of the human or animal body.

Another aspect of the present invention pertains to a drug or prodrug compound as described herein for use in a method of treatment of cancer of the human or animal body.

Another aspect of the present invention pertains to use of a drug or prodrug compound as described herein for the manufacture of a medicament for use in the treatment of cancer.

Another aspect of the present invention pertains to a method for the treatment of cancer comprising administering to a subject suffering from cancer a therapeutically-effective amount of a drug or prodrug compound as described herein.

Another aspect of the present invention pertains to a method for the preparation of a compound according to Formula I or Formula II, as described herein.

DETAILED DESCRIPTION OF THE INVENTION

Accordingly, one aspect of the present invention pertains to a compound of general Formula I:

The compound of Formula I is a prodrug which may be converted into the corresponding active drug of Formula II by cleavage of the amide bond between the residue of $R^6$—$NH_2$ and the benzoic acid nitrogen mustard residue.

Thus, another aspect of the present invention pertains to a compound of general Formula II:

In the above Formulae I and II:
$R^1$ is —Cl, —Br, —I, —OSO$_2$CH$_3$, or —OSO$_2$Ph;
$R^2$ is —Cl, —Br, —I, —OSO$_2$CH$_3$, or —OSO$_2$Ph;
wherein Ph denotes a phenyl group which is optionally substituted with 1, 2, 3, 4 or 5 substituents independently selected from a $C_{1-4}$ alkyl group, —F, —Cl, —Br, —I, —CN, or —NO$_2$;
$R^{1a}$ is —H, a $C_{1-4}$alkyl group, or a $C_{1-4}$haloalkyl group;
$R^{2a}$ is —H, a $C_{1-4}$alkyl group, or a $C_{1-4}$haloalkyl group;
$R^{1b}$ is —H, a $C_{1-4}$alkyl group, or a $C_{1-4}$haloalkyl group;
$R^{2b}$ is —H, a $C_{1-4}$alkyl group, or a $C_{1-4}$haloalkyl group;
$R^3$ is —F, —Cl, —Br, —I, —OCHF$_2$, —C≡CH, —OCF$_3$, —CH$_3$, —CF$_3$, —SF$_5$, —SCF$_3$, or —CF$_2$CF$_3$;
$R^4$ is —H, —F, —Cl, —Br, —I, —OCHF$_2$, —C≡CH, —OCF$_3$, —CH$_3$, —CF$_3$, —SF$_5$, —SCF$_3$, or —CF$_2$CF$_3$;
$R^5$ is —H or —F;
with the proviso that if $R^4$ is —H, then $R^3$ is not —F;
$R^7$ is —H, —C(CH$_3$)$_3$, or —CH$_2$—CH=CH$_2$;
Z is —CH$_2$—T—W;
T is —CH$_2$—, —O—, —S—, —(S=O)—, or —(SO$_2$)—;
the group —CH$_2$—T— may optionally be substituted with 1 or 2 substituents, denoted $Q^1$ and $Q^2$ respectively, on carbon, wherein $Q^1$ and $Q^2$ are independently a $C_{1-4}$alkyl group or a halogen; or, when $Q^1$ and $Q^2$ are bonded to adjacent carbon atoms, $Q^1$ and $Q^2$ together may form a $C_{3-4}$alkylene radical optionally substituted with 1, 2, 3 or 4 substituents independently selected from $C_{1-4}$alkyl groups and halogens;
W is one of:
(1)—COOH;
(2)—(C=O)OR$^8$;
(3)—(C=O)NR$^9$R$^9$;
(4)—SO$_2$NHR$^{10}$;
(5)—SO$_2$OR$^{11}$;
(6)—PO$_3$R$^{11}$R$^{11}$;
(7) a tetrazol-5-yl group:

(8) —CONH—SO$_2$R$^{12}$; and,
(9)-M-Het;
with the proviso that if T is —O—, —S—, —(S=O)—, or —(SO$^2$)—, then W is not —COOH;
$R^8$ is a $C_{1-6}$alkyl group, a $C_{3-6}$cycloalkyl group, a $C_{5-20}$aryl group, or —CH$^2$—CH=CH$_2$;
wherein the $C_{5-20}$aryl group (e.g., -Ph) may optionally be substituted on carbon with from 1 to 4 substituents selected from —COOH, —OH, —NH$_2$, —CH$_2$NH$_2$, —(CH$_2$)$_{1-4}$COOH, tetrazol-5-yl, and —SO$_3$H;

R$^9$ is independently —H, a C$_{1-6}$alkyl group, a C$_{3-6}$cycloalkyl group, a C$_{5-20}$aryl group (e.g., -Ph), a C$_{7-9}$aralkyl group, or a C$_{5-20}$heteroaryl group linked to N via carbon;

wherein C$_{5-20}$heteroaryl is a 5 or 6 membered ring containing 1 to 3 heteroatoms selected from the group consisting of nitrogen and sulphur;

and wherein the C$_{5-20}$aryl group (e.g., -Ph), the C$_{5-20}$heteroaryl group, and aryl moiety of the C$_{7-9}$aralkyl group may optionally be substituted on carbon with from 1 to 4 substituents selected from —COOH, —OH, —NH$_2$, —CH$_2$NH$_2$, —(CH$_2$)$_{1-4}$COOH, tetrazol-5-yl, and —SO$_3$H;

and wherein the C$_{3-6}$cycloalkyl group may optionally carry a methyl group;

R$^{10}$ is a C$_{1-6}$alkyl group, —CH$_2$—CH=CH$_2$, a C$_{3-6}$cycloalkyl group, a C$_{1-4}$haloalkyl group (e.g., —CF$_3$, —CH$_2$CF$_3$), or a C$_{5-20}$aryl group (e.g., phenyl);

wherein the C$_{5-20}$aryl group (e.g., -Ph), the C$_{5-20}$heteroaryl group, and aryl moiety of the C$_{1-9}$aralkyl group may optionally be substituted on carbon with from 1 to 4 substituents selected from —COOH, —OH, —NH$_2$, —CH$_2$NH$_2$, —(CH$_2$)$_{1-4}$COOH, tetrazol-5-yl, and —SO$_3$H;

and wherein the C$_{3-6}$cycloalkyl group may optionally carry a methyl group;

R$^{11}$ represents —H, a C$_{1-6}$alkyl group, or a C$_{3-6}$cycloalkyl group;

R$^{12}$ is one of:

(a) a C$_{3-7}$cycloalkyl group;

(b) a C$_{1-6}$alkyl group, optionally substituted with one or more of: a phenyl group; a phenyl group with from 1 to 5 substituents selected from halogen, —NO$_2$, —CF$_3$, C$_{1-4}$alkyl, C$_{1-4}$alkoxy, —NH$_2$, —NHCOCH$_3$, —CONH$_2$, —OCH$_2$COOH, —NH(C$_{1-4}$alkyl), —N(C$_{1-4}$alkyl)$_2$, —NHCOOC$_{1-4}$alkyl, —OH, —COOH, —CN and —COOC$_{1-4}$alkyl; a C$_{1-4}$alkyl group; a C$_{1-4}$haloalkyl group (e.g., —CF$_3$); or a halogen; and, (c) a C$_{1-6}$perfluoroalkyl group;

M represents —S—, —SO—, or —SO$_2$—; and,

Het represents a 5 or 6 membered heterocyclic aromatic ring linked to M via a carbon atom of the aromatic ring, said aromatic ring containing 1, 2, 3 or 4 heteroatoms selected from the group consisting of O, N and S said aromatic ring optionally being substituted on carbon atoms of the ring with 1, 2, 3 or 4 substituents selected from the group consisting of —OH, —SH, —CN, —CF$_3$, NH$_2$ and halogen.

(1) In one preferred embodiment of the compounds of Formulae I and II:

R$^1$ and R$^2$ are independently —I, —Br, or —Cl; and, the remaining groups are as defined above.

(2) In one preferred embodiment of the compounds of Formulae I and II:

R$^1$ and R$^2$ are both —I; and, the remaining groups are as defined above.

(3) In one preferred embodiment of the compounds of Formulae I and II:

R$^{1a}$, R$^{1b}$, R$^{2a}$, R$^{2b}$ are each independently —H or —CH$_3$; and, the remaining groups are as defined above.

(4) In one preferred embodiment of the compounds of Formulae I and II:

R$^{1a}$, R$^{1b}$, R$^{2a}$, R$^{2b}$ are all —H; and, the remaining groups are as defined above.

(5) In one preferred embodiment of the compounds of Formulae I and II:

R$^1$ and R$^2$ are independently —I, —Br, or —Cl;

R$^{1a}$, R$^{1b}$, R$^{2a}$, R$^{2b}$ are each independently —H or —CH$_3$; and, the remaining groups are as defined above.

(6) In one preferred embodiment of the compounds of Formulae I and II:

R$^1$ and R$^2$ are both —I;

R$^{1a}$, R$^{1b}$, R$^{2a}$, R$^{2b}$ are all —H; and, the remaining groups are as defined above.

(7) In one preferred embodiment of the compounds of Formulae I and II:

R$^3$ and R$^4$ are —CF$_3$, and —H, respectively; and, the remaining groups are as defined above.

(8) In one preferred embodiment of the compounds of Formulae I and II:

R$^3$ and R$^4$ are both —F; and, the remaining groups are as defined above.

(9) In one preferred embodiment of the compounds of Formulae I and II:

R$^3$ and R$^4$ are —CF$_3$ and —H, respectively;

R$^5$ is —H; and, the remaining groups are as defined above.

(10) In one preferred embodiment of the compounds of Formulae I and II:

R$^3$ and R$^4$ are both —F;

R$^5$ is —F; and, the remaining groups are as defined above.

(11) In one preferred embodiment of the compounds of Formulae I and II:

R$^3$ and R$^4$ are both —F;

R$^5$ is —H; and, the remaining groups are as defined above.

(12) In one preferred embodiment of the compounds of Formulae I and II:

R$^1$ and R$^2$ are independently —I, —Br, or —Cl;

R$^{1a}$, R$^{1b}$, R$^{2a}$, R$^{2b}$ are each independently —H or —CH$_3$;

R$^3$ and R$^4$ are —CF$_3$ and —H, respectively, and R$^5$ is —H; or

R$^3$ and R$^4$ are both —F, and R$^5$ is —F; or

R$^3$ and R$^4$ are both —F, and R$^5$ is —H; and, the remaining groups are as defined above.

(13) In one preferred embodiment of the compounds of Formulae I and II:

R$^1$ and R$^2$ are both —I;

R$^{1a}$, R$^{1b}$, R$^{2a}$, R$^{2b}$ are all —H;

R$^3$ and R$^4$ are both —F, and R$^5$ is —F; or

R$^3$ and R$^4$ are both —F, and R$^5$ is —H; and, the remaining groups are as defined above.

(14) In one preferred embodiment of the compounds of Formula I:

R$^7$ is —H, —C(CH$_3$)$_3$, or —CH$_2$—CH=CH$_2$;

Z is —CH$_2$—T—C(=O)OH or —CH$_2$—T—C(=O)OR$^8$, wherein:

T is —CH$_2$— and R$^8$ is as defined above; and, the remaining groups are as defined above.

(15) In one preferred embodiment of the compounds of Formula I:
 $R^7$ is —H or —C(CH$_3$)$_3$;
 Z is —CH$_2$—T—C(=O)OH or —CH$_2$—T—C(=O)OR$^8$, wherein:
  T is —CH$_2$— and R$^8$ is as defined above; and,
 the remaining groups are as defined above.

(16) In one preferred embodiment of the compounds of Formulae I and II:
 $R^3$ and $R^4$ are —CF$_3$ and —H, respectively;
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$, wherein:
  T is —CH$_2$— and R$^8$ is as defined above; and,
 the remaining groups are as defined above.

(17) In one preferred embodiment of the compounds of Formulae I and II:
 $R^3$ and $R^4$ are both —F;
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$, wherein:
  T is —CH$_2$— and R$^8$ is as defined above; and,
 the remaining groups are as defined above.

(18) In one preferred embodiment of the compounds of Formulae I and II:
 $R^3$ and $R^4$ are —CF$_3$ and —H, respectively;
 $R^5$ is —H;
 $R^7$ is —H, —C(CH$_3$)$_3$, or —CH$_2$—CH=CH$_2$;
 Z is —CH$_2$—T—C (=O)OH or —CH$_2$—T—C(=O)OR$^8$, wherein:
  T is —CH$_2$— and R$^8$ is as defined above; and,
 the remaining groups are as defined above.

(19) In one preferred embodiment of the compounds of Formulae I and II:
 $R^3$ and $R^1$ are both —F;
 $R^5$ is —F;
 $R^7$ is —H, —C(CH$_3$)$_3$, or —CH$_2$—CH=CH$_2$;
 Z is —CH$_2$—T—C (=O)OH or —CH$_2$—T—C (=O)OR$^8$, wherein:
  T is —CH$_2$— and R$^8$ is as defined above; and,
 the remaining groups are as defined above.

(20) In one preferred embodiment of the compounds of Formulae I and II:
 $R^3$ and $R^4$ are both —F;
 $R^5$ is —H;
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$, wherein:
  T is —CH$_2$— and R$^8$ is as defined above; and,
 the remaining groups are as defined above.

(21) In one preferred embodiment of the compounds of Formulae I and II:
 $R^1$ and $R^2$ are independently —I, —Br, or —Cl;
 $R^{1a}$, $R^{1b}$, $R^{2a}$, $R^{2b}$ and each independently —H or —CH$_3$;
 $R^3$ and $R^4$ are —CF$_3$ and —H, respectively, and $R^5$ is —H; or
 $R^3$ and $R^4$ are both —F, and $R^5$ is —F; or
 $R^3$ and $R^4$ are both —F, and $R^5$ is —H;
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$ wherein:
  T is —CH$_2$— and R$^8$ is as defined above.

(22) In one preferred embodiment of the compounds of Formulae I and II:
 $R^1$ and $R^2$ are both —I;
 $R^{1a}$, $R^{1b}$, $R^{2a}$, $R^{2b}$ are all —H;
 $R^3$ and $R^4$ are both —F, and $R^5$ is —F; or
 $R^3$ and $R^4$ are both —F, and $R^5$ is —H;
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$, wherein:
  T is —CH$_2$— and R$^8$ is as defined above.

(23) In one preferred embodiment of the compounds of Formula I:
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$, wherein:
  T is —CH$_2$—; and,
  $R^8$ is —H, —C(CH$_3$)$_3$, or —CH$_2$—CH=CH$_2$; and,
 the remaining groups are as defined above.

(24) In one preferred embodiment of the compounds of Formula I:
 $R^7$ is —H or —C(CH$_3$)$_3$;
 Z is —CH$_2$—T—C(=O)OH or —CH$_2$—T—C(=O)OR$^8$, wherein:
  T is —CH$_2$—; and,
  $R^8$ is —H, —C(CH$_3$)$_3$, or —CH$_2$—CH=CH$_2$; and,
 the remaining groups are as defined above.

(25) In one preferred embodiment of the compounds of Formulae I and II:
 $R^3$ and $R^4$ are —CF$^3$ and —H, respectively;
 $R^7$ is —H, —C(CH$_3$) 3, or —CH$_2$—CH=CH$_2$;
 Z is —CH$_2$—T—C((=O)OH or —CH$_2$—T—C(=O)OR$^8$, wherein:
  T is —CH$_2$—; and,
  $R^8$ is —H, —C(CH$_3$)$_3$, or —CH$_2$—CH=CH$_2$; and,
 the remaining groups are as defined above.

(26) In one preferred embodiment of the compounds of Formulae I and II:
 $R^3$ and $R^4$ are both —F;
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$, wherein:
  T is —CH$_2$—; and,
  $R^8$ is —H, —C(CH$_3$)$_3$, or —CH$_2$—CH=CH$_2$; and,
 the remaining groups are as defined above.

(27) In one preferred embodiment of the compounds of Formulae I and II:
 $R^3$ and $R^4$ are —CF$_3$ and —H, respectively;
 $R^5$ is —H;
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$, wherein:
  T is —CH$_2$—; and,
  $R^8$ is —H, —C(CH$_3$)$_3$, or —CH$_2$—CH=CH$_2$; and,
 the remaining groups are as defined above.

(28) In one preferred embodiment of the compounds of Formulae I and II:
 $R^3$ and $R^4$ are both —F;
 $R^5$ is —F;
 $R^7$ is —H, —C(CH$_3$)$_3$, or —CH$_2$—CH=CH$_2$;
 Z is —CH$_2$—T—C(=O)OH or —CH$_2$—T—C(=O)OR$^8$, wherein:

T is —CH$_2$—; and,

R$^8$ is —H, —C(CH$_3$)$_3$, or —CH$_2$—CH=CH$^2$; and, the remaining groups are as defined above.

(29) In one preferred embodiment of the compounds of Formulae I and II:

R$^3$ and R$^4$ are both —F;

R$^5$ is —H;

R$^7$ is —H, —C(CH$_3$)$_3$, or —CH$_2$—CH=CH$_2$;

Z is —CH$_2$—T—C(=O)OH or —CH$_2$—T—C(=O)OR$^8$, wherein:

T is —CH$_2$—; and,

R$^5$ is —H, —C(CH$_3$)$_3$, or —CH$_2$—CH=CH$_2$; and, the remaining groups are as defined above.

(30) In one preferred embodiment of the compounds of Formulae I and II:

R$^1$ and R$^2$ are independently —I, —Br, or —Cl;

R$^{1a}$, R$^{1b}$, R$^{2a}$, R$^{2b}$ are each independently —H or —CH$_3$;

R$^3$ and R$^4$ are —CF$_3$ and —H, respectively, and R$^5$ is —H; or

R$^3$ and R$^4$ are both —F, and R$^5$ is —F; or

R$^3$ and R$^4$ are both —F, and R$^5$ is —H;

R$^7$ is —H, —C(CH$_3$)$_3$, or —CH$_2$—CH=CH$_2$;

Z is —CH$_2$—T—C(=O)OH or —CH$_2$—T—C(=O)OR$^8$, wherein:

T is —CH$_2$—; and,

R$^8$ is —H, —C(CH$^3$)$_3$, or —CH$_2$—CH=CH$_2$.

(31) In one preferred embodiment of the compounds of Formulae I and II:

R$^1$ and R$^2$ are both —I;

R$^{1a}$, R$^{1b}$, R$^{2a}$, R$^{2b}$ are all —H;

R$^3$ and R$^4$ are both —F, and R$^5$ is —F; or

R$^3$ and R$^4$ are both —F, and R$^5$ is —H;

R$^7$ is —H, —C(CH$_3$)$_3$, or —CH$_2$—CH=CH$_2$;

Z is —CH$_2$—T—C(=O)OH or —CH$_2$—T—C(=O)OR$^8$, wherein:

T is —CH$_2$—; and,

R$^8$ is —H, —C(CH$_3$)$_3$, or —CH$_2$—CH=CH$_2$.

In one preferred embodiment, the compound is {3,5—difluoro-4-[bis(2-iodoethyl)amino]benzoyl}-L-glutamic acid, as shown in Example 1(iv).

In one preferred embodiment, the compound is {3,5-difluoro-4-[bis(2-chloroethyl)amino]benzoyl}-L-glutamic acid, as shown in Example 2(ii).

In one preferredembodiment, the compound is {3,5-difluoro-4-[bis(2-bromoethyl)amino]benzoyl}-L-glutamic acid, as shown in Example 3(ii).

In one preferred embodiment, the compound is {2,3,5-trifluoro-4-[bis(2-chloroethyl)amino]benzoyl}-L-glutamic acid, as shown in Example 4(iv).

In one preferred embodiment, the compound is {2,3,5-trifluoro-4-[bis(2-bromoethyl)amino]benzoyl}-L-glutamic acid, as shown in Example 5(ii).

In one preferred embodiment, the compound is {2,3,5-trifluoro-4-[bis(2-iodoethyl)amino]benzoyl}-L-glutamic acid, as shown in Example 6(ii).

In one preferred embodiment, the compound is {3,5-difluoro-4-[bis(2-bromopropyl)amino]benzoyl}-L-glutamic acid, as shown in Example 7(iv).

In one preferred embodiment, the compound is {3-trifluoromethyl-4-[bis(2-bromoethyl)amino]benzoyl}-L-glutamic acid, as shown in Example 8(iv).

Compounds of Formula I in which (a) R$^7$ is other than hydrogen; and, (b) W is —(C=O)—O—R$^8$ where R$^8$ is other than hydrogen (e.g., diesters) are usually made as intermediates in the production of compounds in which R$^7$ and R$^8$ are both H (e.g., diacids), which are preferred for use as prodrugs. This is so as to provide protection of the carboxy groups of the compound during synthesis of the nitrogen mustard moiety, as shown in the Examples below. Removal of such protecting groups is illustrated in the Examples, but is also described in WO 88/07378 and WO 90/02729. Examples of such compounds are discussed below.

In one preferred embodiment, the compound is di-tert-butyl {3,5-difluoro-4-[bis(2-iodoethyl)amino]benzoyl}-L-glutamate, as shown in Example 1(iii).

In one preferred embodiment, the compound is di-tert-butyl {3,5-difluoro-4-[bis(2-chloroethyl)amino]benzoyl}-L-glutamate, as shown in Example 2(i).

In one preferred embodiment, the compound is di-tert-butyl {3,5-difluoro-4-[bis(2-bromoethyl)amino]benzoyl}-L-glutamate, as shown in Example 3(i).

In one preferred embodiment, the compound is di-tert-butyl {2,3,5-trifluoro-4-[bis(2-chloroethyl)amino]benzoyl}-L-glutamate, as shown in Example 4(iii).

In one preferred embodiment, the compound is di-tert-butyl {2,3,5-trifluoro-4-[bis(2-bromoethyl)amino]benzoyl}-L-glutamate, as shown in Example 5(i).

In one preferred embodiment, the compound is di-tert-butyl {2,3,5-trifluoro-4-[bis(2-iodoethyl)amino]benzoyl}-L-glutamate, as shown in Example 6(i).

In one preferred embodiment, the compound is di-tert-butyl {3,5-difluoro-4-[bis(2-bromopropyl)amino]benzoyl}-L-glutamate, as shown in Example 7(iii).

In one preferred embodiment, the compound is di-tert-butyl {3-trifluoromethyl-4-[bis(2-bromoethyl)amino]benzoyl}-L-glutamate, as shown in Example 8(iii).

Salts

It may be convenient or desirable to prepare, purify, and/or handle a corresponding salt of the compounds of Formula I and II, for example, a pharmaceutically-acceptable salt. Examples of pharmaceutically acceptable salts are discussed in Berge et al., 1977.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na+ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, ethylenediamine, ethanolamine, diethanolamine, piperazine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, anions from the following organic acids: acetic, propionic, succinic, gycolic, stearic, lactic, malic, tartaric, citric, ascorbic, pamoic, maleic, hydroxymaleic, phenylacetic, glutamic, benzoic, salicylic, sulfanilic, 2-acetyoxybenzoic, fumaric, toluenesulfonic, methanesulfonic, ethane disulfonic, oxalic, isethionic, and valeric.

Methods of Synthesis

In a further aspect, the present invention provides methods for the preparation of compounds of Formulae I and II.

Compounds of Formula I in which (a) $R^7$ is hydrogen; and, (b) W is —(C=O)—O—$R^8$ where $R^8$ is hydrogen (e.g., diacids) may be prepared from the corresponding compounds, where in (a) $R^7$ is other than hydrogen; and, (b) W is —(C=O)—O—$R^8$ where $R^8$ is other than hydrogen (e.g., diesters). A suitable method is by treatment with a suitable acid, for example in a substantially non-aqueous medium, for example, at room temperature (e.g., at 15–25° C.). Examples of suitable acids include trifluoroacetic acid (TFA) and formic acid (HCOOH). The process may include converting the deprotected compound (e.g., diacid) into a pharmaceutically acceptable salt thereof.

Prodrugs of the invention may thus be produced by processes analogous to those described in WO 88/07378, WO 90/02729 and WO 91/03460.

Bismesyl compounds of the invention, in which $R^1$ and $R^2$ are mesyl (i.e., —$SO_2CH_3$), $R^7$ is not hydroxy, and Z does not include an unprotected hydroxy group may be made from the corresponding di-hydroxy compound by reaction with methane sulphonic anhydride (($CH_3SO_2)_2O$) in $CH_2Cl_2$ and triethylamine ($NEt_3$) at room temperature.

Similarly, optionally substituted phenyl sulphonic anhydride (e.g., ($PhSO_2)_2O$) may be used under similar conditions to provide compounds of the invention in which $R^1$ and $R^2$ are optionally substituted —$OSO2Ph$.

The protected bismesyl compounds described above may be converted into other compounds of the invention in which $R^7$ is —OH and Z includes an unprotected hydroxy group, by deprotection in TFA as described in the examples herein.

Alternatively, the protected bismesyl compounds may be used to provide further compounds of the invention by treatment with an alkali metal halide (e.g., LiCl, LiBr, or NaI) in a suitable solvent (e.g., acetone or N,N-dimethylacetamide) under elevated temperature or under reflux, to cause substitution of one or both mesyl groups by the corresponding halide (X denotes Cl, Br, or I). The resulting compound may be deprotected as above.

Certain compounds of the Formula I may be made by reaction of the corresponding compound of Formula II by reaction with a compound of formula $H_2N$—CH(Z)C(=O)$OR^7$, where Z and $R^7$ are as defined above, in a suitable solvent (e.g., DMF, N,N-dimethylformamide) in the presence of diethyl cyanophosphonate (NC—P(=O)($OCH_2CH_3)_2$) and base.

The benzoic acid compound referred to above may be prepared in any convenient way. A suitable means is by reaction of the corresponding nitrile with a strong base (e.g., NaOH) in an aqueous solvent (e.g., ethanol) under reflux.

The nitrile referred to above may be obtained by reaction of a substituted benzonitrile, where G is a group, such as F or Cl, which is capable of being substituted with (optionally substituted) diethanolamine or protected diethanolamine in a suitable solvent, such as N,N-dimethylacetamide (DMA)

Alternatively, certain compounds of Formula I, where $R^3$, $R^4$ and $R^1$ are all fluoro, $R^7$ is other than OH, and Z does not include an unprotected OH group, may be prepared from the corresponding substituted benzamide, where G is as defined above, by reaction with (optionally substituted) diethanolamine in a suitable solvent such as N,N-dimethylacetamide.

The substituted benzamide referred to above may be obtained by reaction of the corresponding benzoyl chloride, where $R^3$, $R^4$ and $R^5$ are —F, with a compound of formula $H_2N$—CH(Z)C(=O)$OR^7$, with Z and $R^7$ defined above.

The methods described both above and in the Examples below, alone or in combination with other known methods, may be readily adapted by one of ordinary skill in the art to obtain other compounds of the present invention.

Compositions, Systems, Kits, and Uses

The compounds of the present invention, and particularly the prodrugs of Formula I, are suitable for use in a method of treatment of the human or animal body by therapy, particularly a method of treatment of cancer or other conditions in which selective killing of target cells in the body of a patient is required. The animal may be a non-human mammal. The cancer may be any disease in which there is a neoplastic cell growth, including leukemias and solid tumours. Examples of tumours which may be treated in accordance with the present invention include breast, colorectal and ovarian tumours, as well as pancreatic, melanoma, glioblastoma, hepatoma, small cell lung, non-small cell lung, muscle and prostate tumours.

It will be understood by those of skill in the art that the treatment of a tumour includes any measure taken by a physician to alleviate the effect of the tumour on a patient. Thus, although complete remission of the tumour is a desirable goal, effective treatment will also include any measure capable of achieving partial remission of the tumour as well as a slowing down in the rate of growth of a tumour including metastases. Such measures can be effective in prolonging and/or enhancing the quality of life and/or relieving the symptoms of the disease.

The present invention thus extends in various aspects to the use of a prodrug of the invention in a method of medical treatment, particularly a method of treatment of cancer; the use of such a prodrug in the manufacture of a composition for the treatment of a disease, disorder or other medical condition, e.g. in the manufacture of a composition for the treatment of cancer; a method of treating a human or animal patient suffering from cancer, the method comprising administering to the patient a prodrug of the invention in combination with an enzyme-prodrug therapy; and a method of making a pharmaceutical composition comprising admixing a prodrug of the invention with a pharmaceutically acceptable excipient, vehicle or carrier, and optionally other ingredients.

A prodrug of the invention may be selectively converted to the corresponding active drug by the enzyme component of an enzyme-prodrug therapy such as ADEPT, GDEPT or LIDEPT system. Accordingly, the present invention provides a two component system comprising:

(i) a first component capable of delivering a carboxypeptidase enzyme to the interior or exterior of a target cell or a vector encoding said enzyme to the interior of said cell such that said vector expresses said enzyme in said cell, and (ii) a prodrug of Formula I capable of being converted by said enzyme into a drug of Formula II. It will be apparent to those of skill in the art that the first component may be in the form of an antibody or ligand conjugated to the enzyme, or a vector capable of expressing a carboxypeptidase enzyme, or indeed any other suitable form for delivery of the enzyme to the cell such that activation of a prodrug may occur selectively at the site of the cell. Such means are well known and described as such in the prior art mentioned above.

The term "antibody" should be construed as covering antibody derivatives, functional equivalents and homologues of antibodies, including synthetic molecules and molecules whose shape mimics that of an antibody enabling it to bind an antigen or epitope. Thus the term includes monoclonal and polyclonal antibodies, as well as antibody fragments capable of binding an antigen such as Fab fragments, Fv fragments consisting of the VL and VH domains of a single arm of an antibody or single chain Fvs in which said domains are linked by a polypeptide linker.

Examples of suitable ligands include vascular endothelial growth factor (VEGF), epidermal growth factor, EGF, (which binds to epidermal growth factor receptor), heregulin and c-erbB2 ligand. The known VEGF receptors are tyrosine kinases called flt-1 and flk-1, which are specifically expressed in endothelial cells of the tumour and in the border between the tumour and normal tissue. EGFR and c-ErbB2 are expressed in a number of tumour types.

For GDEPT, a wide variety of vectors are available. These include those which are based upon a retrovirus. Such vectors are widely available in the art. Huber et al (ibid) report the use of amphotropic retroviruses for the transformation of hepatoma, breast, colon or skin cells. Culver et al (Science (1992), Vol. 256 pp. 1550–1552) also describe the use of retroviral vectors in GDEPT. Such vectors or vectors derived from such vectors may also be used. Other retroviruses may also be used to make vectors suitable for use in the present invention. Such retroviruses include rous sarcoma virus (RSV). The promoters from such viruses may be used in vectors in a manner analogous to that described above for MLV.

EP-A-415 731 describes molecular chimeras comprising a promoter which may be activated in a tumour cell operably linked to a heterologous gene encoding an enzyme capable of converting a prodrug into a cytotoxic agent. Such molecular chimeras may be used to express carboxypeptidase in tumour cells in order to activate prodrugs of the invention.

EP-A-415 731 describes incorporation of such molecular chimeras into viral vectors, e.g. adenoviral or retroviral vectors. Such viral vectors may also be adapted for utilization in the present invention.

Other recombinant viral vector delivery systems are described in WO 91/02805, WO 92/14829, WO 93/10814, WO 94/21792, WO 95/07994, WO 95/14091 and WO 96/22277. Methods for producing vector delivery systems based on the above-mentioned disclosures may be used to deliver vectors encoding the activating enzyme (e.g. carboxypeptidase) to target cells.

Englehardt et al. (Nature Genetics (1993), Vol. 4, pp. 27–34) describes the use of adenovirus based vectors in the delivery of the cystic fibrosis transmembrane conductance product (CFTR) into cells, and such adenovirus based vectors may also be used in accordance with the present invention. Vectors utilising adenovirus promoter and other control sequences may be of use in delivering a system according to the invention to cells in the lung, and hence useful in treating lung tumours.

Vectors encoding the carboxypeptidase may be made using recombinant DNA techniques known per se in the art. The sequences encoding the enzyme may be constructed by splicing synthetic or recombinant nucleic acid sequences together, or modifying existing sequences by techniques such as site directed mutagenesis. Reference may be made to "Molecular Cloning" by Sambrook et al (1989, Cold Spring Harbor) for discussion of standard recombinant DNA techniques. In general, the vector may be any DNA or RNA vector used in GDEPT therapies.

The carboxypeptidase will be expressed from the vector using a promoter capable of being expressed in the cell to which the vector is targeted. The promoter will be operably linked to the sequences encoding the enzyme and its associated sequences.

Suitable promoters include viral promoters such as mammalian retrovirus or DNA virus promoters, e.g. MLV, CMV, RSV and adenovirus promoters. Preferred adenovirus promoters are the adenovirus early gene promoters. Strong mammalian promoters may also be suitable. An example of such a promoter is the EF-1α promoter which may be obtained by reference to Mizushima and Nagata (Nucl. Acids Res. (1990), Vol. 18, p. 5322). Variants of such promoters retaining substantially similar transcriptional activities may also be used.

The c-erbB2 proto-oncogene is expressed in breast tissues at low levels and in a tissue restricted manner. In some tumour states, however, the expression of this protein in increased, due to enhanced transcriptional activity. Notable examples of this are breast tissue (about 30% of tumours), ovarian (about 20%) and pancreatic tumours (about 50–75%). In such tumours where expression of c-erbB2 is increased due to enhanced transcription or translation, the c-erbB2 promoter may be used to direct expression of the activating enzyme in a cell specific manner. The specificity of GDEPT may be increased since transfection of normal cells by a vector with a c-erbB2 promoter will provide only very limited amount of enzyme or none and thus limited activation of prodrug. The use of the c-erbB2 promoter and homologous promoters in GDEPT is more fully described in WO 96/03151.

A carboxypeptidase enzyme of the invention will be any suitable carboxypeptidase enzyme capable of cleaving the glutamic acid or glutamic acid derivative moiety of compounds of the Formula I. Preferred carboxypeptidase enzymes are bacterial carboxypeptidases, particularly carboxypeptidase G enzymes including CPG1, 2 or 3. A pseudomonad carboxypeptidase enzyme is described in Levy and Goldman, J. Biol. Chem., 1967, 12, 2933–2938. CPG1 is described by Cornell and Charm, Biotechnology and Bioengineering, Vol XVIII, 1976, 1171–1173. CPG2 is described in WO 88/07378 and CPG3 is described by Yasuda et al, Bull. Mukogawa, Women's Univ. Nat. Sci, 1994, 42, 63–66. Although naturally occurring carboxypeptidase enzymes are preferred as a matter of convenience, synthetic variants of such enzymes may be made. For example, WO 96/03515 described synthetic variants in which one or more of the glycosylation motifs (Asn-Xaa-Ser/Thr) (where Xaa is any amino acids) are altered to prevent glycosylation. For example, within the primary amino acid sequence of CPG2, there are three such consensus motifs, located at residues Asn 222, Asn 264 and Asn 272. Alteration of one or more of these sites is preferred when CPG2 is used in the present invention. Desirably, the alteration is substitution to leucine or glutamine. Such modifications may also be made in the practice of the present invention.

Other variants of naturally occurring sequences may also be made provided such variants retain carboxypeptidase activity. For example, variants with amino acid sequences having at least 50%, preferably 60% more preferably 70%, 80%, 85%, 90% or 95% amino acid identity may be used. Amino acid identity may be determined by standard algorithms available in the art such as the BLAST algorithms using default parameters.

Where variations of the naturally occurring sequences are made these will be such that the enzyme retains it ability to convert the prodrugs of the invention to their corresponding active drugs at substantially the same rate as the unchanged, unglycosylated enzyme. In this context, "substantially unchanged" will desirably be within 1 order of magnitude, and preferably from about 2-fold less to 2 or 5 fold more.

Carboxypeptidase enzymes may be isolated from natural sources or produced recombinantly, for example, as described in WO 96/03515.

The carboxypeptidase may be expressed as a fusion with a signal sequence which directs the enzyme to the surface of a cell. Such a system is described in WO 96/03515.

Prodrugs of the present invention may also be used as reagents in in vitro systems to test the activity of candidate carboxypeptidase enzymes for incorporation into ADEPT, LIDEPT or GDEPT systems or to test cells such as biopsy samples for their suitability for treatment with an enzyme prodrug system.

Such model systems may also be used to test the toxicity, activity or selectivity of compounds of the present invention against a range of tumour cell types. Suitable tumour cells for use in these model systems include ovarian, colon, glioma, breast, small cell and non-small cell lung cancer cells, and melanomas.

In a further aspect, the present invention provides a pharmaceutical composition, medicament, drug or other composition comprising a prodrug of the invention. The composition may include a pharmaceutically acceptable carrier or diluent.

The invention also provides a kit comprising:
(a) a prodrug of the invention; and,
(b) one of:
  (i) an immunoglobulin/enzyme fusion protein or conjugate in which the immunoglobulin is specific for a cellular (e.g., tumour-associated) antigen and the enzyme is a carboxypeptidase enzyme;
  (ii) a ligand/enzyme conjugate or fusion protein, the ligand being specific for a cellular (e.g., tumour associated) antigen and the enzyme is a carboxypeptidase enzyme;
  (iii) a vector which encodes a carboxypeptidase enzyme which can be expressed in a cell (e.g. tumour cell).

In the kits of the invention, the vectors conjugates or fusion proteins may themselves be provided in a composition including a pharmaceutically acceptable carrier or diluent. Optionally, the kit may include suitable instructions for its use.

Compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise mature of the carrier or other material will depend on the route of administration, which may be oral, or by injection, e.g. cutaneous, subcutaneous or intravenous.

For intravenous, cutaneous or subcutaneous injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection or Lactated Ringer's Injection. Preservatives, stabilisers, buffers, antioxidants and/or other additives may be included, as required.

In ADEPT, the prodrug will normally be administered parenterally, e.g. intravenously or intraperitoneally. Thus, the pharmaceutical composition of the invention may be one which is suitable for parenteral administration. Such a composition conveniently contains the prodrug and isotonic saline or bicarbonate as diluent.

GDEPT will normally involve parenteral administration of both the prodrug and the vector encoding the carboxypeptidase enzyme. Administration by the intravenous route is frequently found to be the most practical. For glioblastoma the route is often intratumoural.

Liposomes containing the vector may be administered by injection in a sterile solution. Viruses may be isolated from packaging cell lines and may be administered by regional perfusion or direct intratumoural injection, or direct injection into a body cavity (intracaviterial administration), for example by intra-peritoneum injection.

Compositions according to the present invention, and for use in accordance with the present invention, may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Injection solutions and suspensions may be prepared extemporaneously from sterile powders, granules and tablets of the kind previously described.

Administration of the prodrug and/or vector and/or fusion and/or conjugate is preferably in a "therapeutically effective amount", that being sufficient to show benefit to the patient. The doses of each component and the route and time-course of their administration will ultimately be at the discretion of the physician, who will take into account such factors as the nature and severity of what is being treated and the age, weight and condition of the patient.

Suitable doses of prodrug and conjugate for the ADEPT approach are given in Bagshawe et al. Antibody, Immunoconjugates, and Radiopharmaceuticals (1991), Vol. 4, pp. 915–922. A suitable dose of conjugate may be from 2000 to 200,000 enzyme units/m$^2$ (e.g. 20,000 enzyme units/m$^2$) and a suitable dose of prodrug may be from 20 to 2000 mg/m$^2$ (e.g. 200 mg/m$^2$)

In order to secure maximum concentration of the fusion protein or conjugate at the site of desired treatment, it is normally desirable to space apart administration of the two components by at least 4 hours. The exact regime will be influenced by various factors including the nature of the tumour to be targeted and the exact nature of the prodrug. A typical regime is to administer the conjugate at 0 h, galactosylated clearing antibody at 24 h, and prodrug at 48 h. If no clearing antibody is used, it would generally be longer than 48 h before the prodrug could be injected.

In using the LIDEPT systems of the present invention the prodrug will usually be administered following administration of the ligand-enzyme fusion protein or conjugate. Typically, the ligand/enzyme will be administered to the patient, and its uptake monitored, for example by recovery and analysis of a biopsy sample of targeted tissue or by injecting trace-labelled protein ligand enzyme.

In using the GDEPT system the prodrug may be administered following administration of the vector encoding the activating enzyme. Typically, the vector will be administered to the patient and then the uptake of the vector by transfected or infected (in the case of viral vectors) cells monitored, for example by recovery and analysis of a biopsy sample of targeted tissue.

The amount of vector delivered will be such as to provide an effective cellular concentration of enzyme so that the prodrug may be activated in sufficient concentration at the site of a tumour to achieve a therapeutic effect, e.g. reduction in the tumour size. This may be determined by clinical trials which involve administering a range of trial doses to a patient and measuring the degree of infection or transfection of a target cell or tumour. The amount of prodrug required will be similar to or greater than that for ADEPT systems of the type mentioned above.

A treatment according to the present invention may be administered alone or in combination with other treatments, either simultaneously or sequentially dependent upon the condition to be treated.

EXAMPLES

The following are examples are provided solely to illustrate the present invention and are not intended to limit the scope of the invention, as described herein.

Example 1

(i) 3,5-difluoro-4-[bis(2-hydroxyethyl)amino]benzonitrile

A solution of 3,4,5-trifluorobenzonitrile (5 g, 32 mmol) and diethanolamine (6 ml, 85 mmol) in N,N-dimethylacetamide was stirred for 10 days. The solvent was then evaporated, the residue partitioned between $CH_2Cl_2$ (200 ml) and $H_2O$ (200 ml), the organic layer dried ($MgSO_4$) and evaporated to dryness. The residue was chromatographed using $CH_2Cl_2$-EtOAc as eluent to give, after recrystallization from toluene, 2.7 g (35%) of pure white crystals: mp 63–65° C.; $^1$H NMR δ3.33 (t, 4H, $NCH_2$, J=6 Hz), 3.48 (t, 4H, $OCH_2$, J=6 Hz), 4.43 (bs, 2H, OH), 7.57 (dd, 2H, H2+6, $J_{H2, F3\,and\,H6, F5}$=8.5 Hz, $J_{H2, F5\,and\,H6, F3=2Hz}$=22 Hz); $^{19}$F NMR δ –116.0 (d, 2F, F3+5, $J_{F3, H2\,and\,F5, 6}$=7.5 Hz); MS m/z 265 (M+Na$^+$, 10), 243 (M+H$^+$, 100), 211 (M-$CH_2OH$, 85). Anal. ($C_{11}H_{12}N_2O_2F_2$) C,H,N.

(ii) 3.5-difluoro-4-[bis(2-hydroxyethyl)amino]benzoic acid

A solution of the 3.5-Difluoro-4-[bis(2-hydroxyethyl) amino]benzonitrile (3.15 g, 13 mmol) and NaOH (5.2 g, 0.13 mol) in aqueous ethanol (65 ml, 50%) was refluxed for 2.5 hours. The solution was then partitioned between EtOAc (800 ml) and HCl (330 ml, 0.4 M), the aqueous layer washed with EtOAc (3×150 ml), the combined organic layers dried ($MgSO_4$) and evaporated to dryness. The solid recrystallized from EtOAc (100 ml) to give 2.94 g (87%) of pure white crystals: mp 146.5–150° C.; $^1$H NMR δ 3.3 (t, 4H, $CH_2N$), 3.46 (q, 4H, $CH_2O$, J=5.5 Hz), 4.49 (t, 2H, OH, J=5 Hz), 7.44 (d, 2H, H2+6, J=10.5 Hz), 13.1 (bs, 1H, $CO_2H$); $^{19}$F NMR δ –117.3 (d, 2F, F3+5, J=9.5 Hz); MS m/z 284 (M+Na$^+$, 15), 262 (M+H$^+$, 100), 230 (M-$CH_2OH$, 40). Anal. ($C_{11}H_{13}NO_4F_2$) C,H,N.

(iii) di-tert-butyl {3,5-difluoro-4-[bis(2-iodoethyl)amino]benzoyl}-L-glutamate a) To a solution of di-tert-butyl-L-glutamate hydrochloride (2.66 g, 9.0 mmol) in dry dimethylformamide (135 ml) was added $Et_3N$ (2.5 ml, 18 mmol), the 3,5-Difluoro-4-[bis(2-hydroxyethyl)amino]benzoic acid (2.35 g, 9.0 mmol) followed by diethylcyanophosphonate (1.5 ml, 9.9 ml). After stirring for 3 days the solvent was evaporated and the residue partitioned between EtOAc (450 ml) and $H_2O$ (375 ml). The organic layer was washed with citric acid (180 ml, 10%), sat. sodium bicarbonate solution (180 ml), dried ($MgSO_4$) and evaporated to dryness, giving 5.6 g of the bis-hydroxy compound.

b) To a solution of the bis-hydroxy compound in dry $CH_2Cl_2$ (165 ml) was added 4-dimethylaminopyridine (0.22 g, 1.8 mmol) and $Et_3N$ (6.3 ml, 45 mmol). This solution was cooled in ice, methane sulphonic anhydride (6.3 g, 36 mmol) dissolved in dry $CH_2Cl_2$ was added over a few minutes and the reaction was allowed to warm up to room temperature. After 16 hr $CH_2Cl_2$ (150 ml) was added, the solution extracted with 10% aqueous citric acid (375 ml), dried ($MgSO_4$) and evaporated to dryness to give the bis-mesyl compound as a brown oil.

c) A solution of the bis-mesyl compound and NaI (13.5 g, 0.09 mol) in acetone (150 ml) was refluxed for 5 hr. The solvent was removed by evaporation, the residue partitioned between $CH_2Cl_2$ (375 ml) and $H_2O$ (375 ml), the organic layer dried ($MgSO_4$) and evaporated to dryness. The impure product was purified on silica using $CH_2Cl_2$ as eluent giving 5.6 g (86%) of pure bis-iodo ester. $^1$H NMR δ 1.39+1.41 (2s, 18H, tert-Bu), 2.0 (m, 2H, $CH_2CH$), 2.33 (t, 2H, $CH_2CO$), 3.3 (t, 4H, $CH_2I$), 3.57 (t, 4H, $CH_2N$, J=7 Hz), 4.3 (m, 1H, CH), 7.6 (d, 2H, H2+6, J=10 Hz), 8.60 (d, 1 H, NH, J=7.5 Hz); $^{19}$F NMR δ –117.2 (d, 2F, F3+5, J=10 Hz).

(iv) {3,5-difluoro-4-[bis(2-iodoethyl)amino]benzoyl}-L-glutamic acid

The bis-iodo ester (5.6 g, 7.8 mmol) was dissolved in trifluoroacetic acid (TFA) (140 ml). After one hour the solvent was removed by evaporation and the residue evaporated six times with EtOAc to remove TFA. The oil was re-dissolved in EtOAc, toluene was added and the solvent partly evaporated. The acid crystallized as a pure white solid (4.5 g, 95%): mp 121–123° C.; $^1$H NMR δ 1.95+2.05 (2m, 2H, CH$_2$CH), 2.34 (t, 2H, CH$_2$CO, J=7.5 Hz), 3.3 (t, 4H, CH$_2$I), 3.57 (t, 4H, CH$_2$N, J=7 Hz), 4.4 (m, 1H, CH), 7.6 (d, 2H, H2+6, J=10 Hz), 8.6 (d, 1H, NH, J=7.5 Hz), 12.5 (bs, 1H, CO$_2$H); $^{19}$F NMR δ -117.2 (d, 2F, F3+5, J=10 Hz); MS m/z 633 (M+Na$^+$, 23), 611 (M+H$^+$, 40), 464 (M-glu, 82). Anal. (C$_{16}$H$_{18}$N$_2$O$_5$F$_2$I$_2$) C,H,N.

Example 2

(i) di-tert-butyl {3,5-difluoro-4-[bis(2-chloroethyl)amino]benzoyl}-L-glutamate

The bis-mesyl compound of Example 1(iii) (c), 2 mmol, was dissolved in N,N-dimethyl acetamide (35 ml) containing LiCl (0.85 g, 20 mmol) and heated at 85° C. for 45 minutes. The solvent was removed by evaporation and the residue partitioned between CH$_2$Cl$_2$ (100 ml) and H$_2$O (30 ml). The organic layer was dried (MgSO$_4$), evaporated to dryness and the residue chromatographed using CH$_2$Cl$_2$ as eluent to give 1.11 g of product.

(ii) {3,5-difluoro-4-[bis(2-chloroethyl)amino]benzoyl}-L-glutamic acid

The product of Example 2(i) was dissolved in 28 ml TFA and treated as in Example 1(iv) to provide 0.88 g of crystalline product.

$^1$H NMR δ 1.95+2.05 (2m, 2H, CH$_2$CH), 2.35 (t, 2H, CH$_2$CO$_2$, J=7.5 Hz), 3.57 (t, 4H, CH$_2$N, J=6 Hz), 3.68 (t, 4H, CH$_2$Cl, J=6 Hz), 4.4 (m, 1H, CH), 7.60 (d, 2H, H2+6, J=10 Hz), 8.61 (d, 1H, NH, J=7.5 Hz); $^{19}$F NMR δ -117.44 (d, 2F, F3+5, J=10 Hz); MS m/z 449 (M+Na$^+$, 17), 427 (M+H$^+$, 51), 377 (M-CH$_2$Cl, 42), 280 (M-glu, 100). Anal. (C$_{16}$H$_{18}$N$_2$O$_5$F$_2$Cl$_2$.0.5toluene) C,H,N.

Example 3

(i) di-tert-butyl {3,5-difluoro-4-[bis(2-bromoethyl)amino]benzoyl}-L-glutamate

The bis-mesyl compound of Example 1(iii) (c), 0.9 mmol, was dissolved in acetone (15 ml) containing LiBr (0.75 g, 9 mmol) and refluxed for 5 hours. The solvent was removed by evaporation and the residue partitioned between CH$_2$Cl$_2$ (30 ml) and H$_2$O (15 ml). The organic layer was dried (MgSO$_4$), and evaporated to dryness. The residue was chromatographed using CH$_2$Cl$_2$-EtOAc as eluent to give 0.4 g of product.

(ii) {3,5-difluoro-4-[bis(2-bromoethyl)amino]benzoyl}-L-glutamic acid

The product of Example 3(i) was dissolved in 10 ml TFA and treated as in Example 1(iv) to provide 0.32 g of crystalline product.

$^2$H NMR δ 1.95+2.05 (2m, 2H, CH$_2$CH), 2.35 (t, 2H, CH$^2$CO$_2$, J=7.5 Hz), 3.55 (t, 4H, CH$^2$N, J=5.5 Hz), 3.61 (t, 4H, CH$_2$Br, J=5.5 Hz), 4.4 (1H, m, CH), 7.60 (d, 2H, H2+6, J=10 Hz), 8.62 (d, 1H, NH, J=7.5 Hz); $^{19}$F NMR δ -117.32 (d, 2F, F3+5, J=10 Hz); MS m/z 539 (M+Na$^+$, 24), 517 (M+H$^+$, 59), 423 (M-CH$_2$Br, 33), 370 (M-glu, 100). Anal. (C$_{16}$H$_{18}$N$_2$O$_5$F$_3$Cl$_2$.0.32toluene) C,H, N.

Example 4

(i) di-tert-butyl (2,3,4,5-tetrafluorobenzoyl)-L-glutamate

To an ice-cold solution of di-tert-butyl L-glutamate hydrochloride (6.6 g, 22.4 mmol) and Et$_3$N (6.9 ml, 50 mmol) in dry CH$_2$Cl$_2$ (70 ml) was added, over a period of 1.5 hr, 2,3,4,5-tetrafluorobenzoyl chloride (5.0 g, 23.5 mmol) in dry CH$_2$Cl$_2$ (20 ml) and thirty minutes later the solution was allowed to warm to room temperature. Sixteen hours later the solution was washed with H₂O, dried (MgSO₄) and evaporated to dryness. ¹H NMR δ 1.40+1.42 (2s, 18H, t-butyl), 1.85+1.95 (2m, 2H, CH₂CH), 2.34 (t, 2H, CH2CO, J=7.5 Hz), 4.3 (m, 1H, CH), 7.57 (m, 1H, H6), 8.80 (d, 1H, NH, J=7.5 Hz); ¹⁹F NMR δ −138.6+139.0 (2m, 2F, F2+5), −152.4 (m, 1H, F4), −154.9 (t, 1F, F3, J=20 Hz).

(ii) di-tert-butyl {4-[bis(2-hydroxyethyl)amino]-2,3,5-trifluorobenzoyl}-L-glutamate A solution of the tetrafluoroamide (4.35 g, 10 mmol) and diethanolamine (3.0 ml, 30 mmol) in N,N-dimethylacetamide (50 ml) was heated at 130° C. with stirring for 2.5 days. The solvent was removed by evaporation and the residue partitioned between CH₂Cl₂ (150 ml) and H₂O (150 ml). The organic layer was dried (MgSO4), evaporated to dryness and chromatographed using CH₂Cl₂-EtOAc as eluent to give 2.7 g (52%) of product.

¹H NMR 1.39+1.41 (2s, 18H, t-butyl), 1.95 (m, 2H, CH₂CH), 2.32 (t, 2H, CH₂CO₂, J=7.5 Hz), 3.3 (t, 4H, CH₂N), 3.49 (q, 4H, CH₂O, J=5.5 Hz), 4.3 (m, 1H, CH), 4.52 (t, 2H, OH, J=5 Hz), 7.18 (q, 1H, H-6), 8.48 (d, 1H, NH, J=7.5 Hz); ¹⁹F NMR δ −122.7 (t, 1F, F5), −142.0 (m, 2F, F2+3).

(iii) di-tert-butyl {4-[bis(2-chloroethyl)amino]-2,3,5-trifluorobenzoyl)-L-glutamate a) A solution of the bis-hydroxy compound (2.6 g, 5.0 mmol), 4-dimethylaminopyridine (90 mg, 0.7 mmol) and Et₃N (2.5 ml, 17.5 mmol) in dry CH₂Cl₂ (70 ml) was cooled in ice. Methane sulphonic anhydride (2.5 g, 14 mmol), dissolved in dry CH₂Cl₂ (20 ml), was added over two minutes and the solution was allowed to warm up to room temperature. After 16 hr CH₂Cl₂ (100 ml) was added and the solution was extracted with 10% aqueous citric acid, dried (MgSO₄) and evaporated to dryness to give the bis-mesyl compound as an oil (3.8 g)

b) The bis-mesyl compound was dissolved in N,N-dimethylacetamide (25 ml) containing LiCl (0.5 g, 10 mmol). After 16 hr the solvent was removed by evaporation and the residue partitioned between CH₂Cl₂ (50 ml) and H₂O (20 ml). The organic layer was dried (MgSO₄), evaporated to dryness and the residue chromatographed using CH₂Cl₂ as eluent to give 1.35 g (97%) of the bis-chloro ester, as a colourless oil.

(iv) 4-[bis(2-chloroethyl)amino]-2,3,5-trifluorobenzoyl-L-glutamic acid

The bis-chloro ester (1.27 g, 2.3 mmol) was dissolved in TFA (30 ml). After one hour the solvent was evaporated and the residue evaporated five times with EtOAc. The product was re-dissolved in EtOAc, toluene was added and the solution evaporated to low volume. More toluene was added and the solution partially evaporated again giving a large mass of white crystals (1.015 g, 97.5%): mp 110° C.; ¹H NMR δ 1.9+2.05 (2m, 2H, CH₂CH), 2.34 (t, 2H, CH₂CO, J=7.5 Hz), 3.60 (t, 4H, CH₂N, J=6 HZ), 3.71 (t, 4H, CH₂Cl, J=6 HZ), 4.4 (m, 1H, CH), 7.25 (m, 1H, H6), 8.56 (d, 1H, NH, J=8 Hz); ¹⁹F NMR δ −122.67 (t, 1F, F5, $J_{F2,5}$=13.5 Hz), −141.3 (m, 1F, F2), −141.5 (d, 1F, F3, $J_{F2,3}$=19 Hz); MS m/z 467 (M+Na⁺,40), 445 (M+H⁺, 82), 395 (M-CH₂Cl, 41), 298 (M-glu, 100). Anal. (C₁₈H₁₇N₂O₅F₃Cl₂0.08toluene) C,H,N.

Example 5

(i) di-tert-butyl {4-[bis(2-bromoethyl)amino]-2,3,5-trifluorobenzoyl}-L-glutamate The bis-mesyl compound of Example 4(iii)(b), 3 mmol, was dissolved in acetone (25 ml) containing LiBr (0.87 g, 10 mmol) and refluxed for 5 hours. The solvent was removed by evaporation and the residue partitioned between CH₂Cl₂ (50 ml) and H₂O (20 ml). The organic layer was dried (MgSO₄), evaporated to dryness and the residue chromatographed using CH₂Cl₂ as eluent to give 1.33 g of product.

(ii) {4-[bis(2-bromoethyl)amino]-2,3,5-trifluorobenzoyl}-L-glutamic acid

The product of Example 5(i) was dissolved in 30 ml TFA and treated as in Example 4(iv) to provide 1.0 g of crystalline product.

¹H NMR δ 1.90+2.05 (2m, 2H, CH₂CH), 2.35 (t, 2H, CH₂CO₂, J=7.5 Hz), 3.58 (t, 2H, CH₂N, J=5.5 Hz), 3.66 (t, 4H, CH₂Br, J=5.5 Hz), 4.4 (m, 1H, CH), 7.25 (dd, 1H, H6, $J_{H5,F5}$=12 Hz, $J_{H6,F3}$=5.5 Hz), 8.56 (d, 1H, NH, J=7.5 Hz);

$^{19}$F NMR δ −122.4 (m, 1F, F5), −141.5 (m, 2F, F2+3); MS m/z 557 (M+Na$^+$, 31), 535 (M+H$^+$, 70), 455 (M-Br, 14), 441 (M-CH$_2$Br, 30), 388 (M-glu, 100). Anal. (C$_{16}$H$_{17}$N$_2$O$_5$F$_3$Br$_2$. 0.06toluene) C,H,N.

Example 6

(i) di-tert-butyl {4-[bis(2-iodoethyl)amino]-2, 3, 5-trifluorobenzoyl}-L-glutamate The bis-mesyl compound of Example 4(iii) (b), 1 mmol, was dissolved in acetone (15 ml) containing NaI (1.5 g, 10 mmol) and refluxed for 5 hours. The solvent was removed by evaporation and the residue partitioned between CH$_2$Cl$_2$ (45 ml) and H$_2$O (15 ml). The organic layer was dried (MgSO$_4$), evaporated to dryness and the residue chromatographed on silica using CH$_2$Cl$_2$ as eluent to give 0.7 g of product.

(ii) {4-[bis(2-iodoethyl)amino]-2,3,5-trifluorobenzoyl}-L-glutamic acid

The product of Example 6(i) was dissolved in 17 ml TFA and treated as in Example 4(iv) to provide 0.53 g of crystalline product.

$^1$H NMR δ 1.9+2.05 (2m, 2H, CH$_2$CH), 2.34 (t, 2H, CH$_2$CO$_2$, J=7.5 Hz), 3.3 (t, 4H, CH$_2$I), 3.59 (t, 4H, CH$_2$N, J=7 Hz), 4.38 (m, 1H, CH), 7.28 (dd, 1H, H6, J$_{H6, F5}$=12 Hz, J$_{H6, F3}$=2.5 Hz), 8.52 (d, 1H, NH, J=7.5 Hz); $^{19}$F NMR −122.7 (t, 1F, F5, J$_{F5, H6}$=14 Hz), −141.3 (m, 2F, F2+3); MS m/z 651 (M+Na$^+$, 23), 629 (M+H+, 65), 482 (M-glu, 100). Anal. (C$_{16}$H$_{17}$N$_2$O$_5$F$_3$I$_2$.0.05toluene) C,H,N.

Example 7

(i) 3,5-difluoro-4-[bis(2-hydroxypropyl)amino]benzonitrile

A solution of 3,4,5-trifluorobenzonitrile (6.3 g, 40 mmol) and diisopropanolamine (13.3 g, 0.1 mol) in N,N-dimethylacetamide (140 ml) was stirred for 3 days at 70° C. The solvent was evaporated, the residue partitioned between CH$_2$Cl$_2$ (250 ml) and H$_2$O (250 ml), the organic layer dried (MgSO$_4$) and evaporated to dryness. The residue was chromatographed using CH$_2$Cl$_2$-EtOH as eluent.

(ii) 3,5-difluoro-4-[bis(2-hydroxypropyl)amino]benzoic acid

A solution of the 3,5-difluoro-4-[bis(2-hydroxypropyl)amino]benzonitrile and NaOH (8 g, 0.2 mol) in aqueous ethanol (100 ml, 50%) was refluxed for 2.5 hours. The solution was partitioned between EtOAc (1.2 l) and HCl (500 ml, 0.4 M), the aqueous layer washed with EtOAc (3×240 ml), the combined organic layers dried (MgSO$_4$) and evaporated to dryness. The residue was chromatographed using CH$_2$Cl$_2$-EtOH-ACOH as eluent.

(iii) di-tert-butyl (3,5-difluoro-4-[bis(2-bromopropyl)amino]benzoyl}-L-glutamate a) To a solution of di-tert-butyl-L-glutamate hydrochloride (0.96 g) in dry dimethylformamide (50 ml) was added Et$_3$N (0.9 ml, 6.4 mmol), the 3,5-difluoro-4-[bis(2-hydroxypropyl)amino]benzoic acid (0.93 g, 3.2 mmol) followed by diethyl cyanophosphonate (0.5 ml, 3.5 mmol). After 2 days the solvent was evaporated and the residue partitioned between EtOAc (150 ml) and H$_2$O (125 ml). The organic layer was washed with citric acid (60 ml, 10%), saturated sodium bicarbonate solution (60 ml), dried (MgSO$_4$), and evaporated to dryness, giving the bis-hydroxy compound.

b) To a solution of the bis-hydroxy compound in dry CH$_2$Cl$_2$ (55 ml) was added 4-dimethylaminopyridine (73 mg, 0.6 mmol) and Et$_3$N (2.1 ml, 15 mmol). This solution was cooled in ice, methane sulphonic anhydride (2.1 g, 12 mmol) dissolved in dry CH$_2$Cl$_2$ (18 ml) was added over a few minutes and the reaction mixture was allowed to warm up to room temperature. After a few hours CH$_2$Cl$_2$ (50 ml) was added, the solution extracted with 10% aqueous citric acid (125 ml), dried (MgSO$_4$), and evaporated to dryness to give the bis-mesyl compound as an oil.

c) A solution of the bis-mesyl compound and LiBr (2.61 g, 30 mmol) in acetone (50 ml) was refluxed for 5 hr. The solvent was removed by evaporation, the residue partitioned between CH$_2$Cl$_2$ (125 ml) and H$_2$O (125 ml), the organic layer dried (MgSO$_4$), and evaporated to dryness. The impure product was purified on silica using CH$_2$Cl$_2$ as eluent, to give the bis-bromo ester.

(iv) {3,5-difluoro-4-[bis(2-bromopropyl)amino]benzoyl}-L-glutamic acid

The bis-bromo ester was dissolved in TFA (15 ml). After 50 minutes, the solvent was removed by evaporation and the residue evaporated four times with EtOAc to remove TFA. The oil was re-dissolved in EtOAc, toluene was added and the solvent partly evaporated. The acid crystallized as a pure white solid.

Example 8

(i) 3-trifluoromethyl-4-[bis(2-hydroxyethyl)amino]benzonitrile

A solution of 3-trifluoromethyl 4-fluoro-benzonitrile (9.45 g, 50 mmol) and diethanolamine (15.8 g, 0.15 mol) in N,N-dimethylacetamide (200 ml) was stirred for 7 days at 50° C. The solvent was evaporated, the residue partitioned between $CH_2Cl_2$ (400 ml) and $H_2O$ (400 ml), the organic layer dried ($MgSO_4$) and evaporated to dryness. The residue was chromatographed using $CH_2Cl_2$-EtOH as eluent.

(ii) 3-trifluoromethyl-4-[bis(2-hydroxyethyl) amino]benzoic acid

A solution of the 3-trifluoromethyl-4-[bis(2-hydroxyethyl) amino]benzonitrile and NaOH (0.8 g, 0.02 mol) in aqueous ethanol (10 ml, 50%) was refluxed for 2 hours. The solution was partitioned between EtOAc (120 ml) and HCl (50 ml, 0.4 M), the aqueous layer washed with EtOAc (3×25 ml), the combined organic layers dried ($MgSO_4$) and evaporated to dryness. The residue was recrystallized from EtOAc to give 0.39 g of white crystals.

(iii) di-tert-butyl (3-trifluoromethyl-4-[bis(2-bromoethyl)amino]benzoyl)-L-glutamate a) To a solution of di-tert-butyl-L-glutamate hydrochloride (0.3 g) in dry dimethylformamide (15 ml) was added $Et_3N$ (0.28 ml, 2 mmol), the 3-trifluoromethyl-4-[bis(2-hydroxyethyl)amino]benzoic acid (0.29 g, 1 mmol) followed by diethyl cyanophosphonate (0.17 ml, 1.1 mmol). After 2 days the solvent was evaporated and the residue partitioned between EtOAc (50 ml) and $H_2O$ (40 ml). The organic layer was washed with citric acid (20 ml, 10%), saturated sodium bicarbonate solution (20 ml), dried ($MgSO_4$), and evaporated to dryness, giving the bis-hydroxy compound.

b) To a solution of the bis-hydroxy compound in dry $CH_2Cl_2$ (6 ml) was added 4-dimethylaminopyridine (7 mg, 0.06 mmol) and $Et_3N$ (0.21 ml, 1.5 mmol). This solution was cooled in ice, methane sulphonic anhydride (0.21 g, 1.2 mmol) dissolved in dry $CH_2Cl_2$ (2 ml) was added over a few minutes and the reaction mixture was allowed to warm up to room temperature. After a few hours $CH_2Cl_2$ (5 ml) was added, the solution extracted with 10% aqueous citric acid (12 ml), dried ($MgSO_4$), and evaporated to dryness to give the bis-mesyl compound as an oil.

c) A solution of the bis-mesyl compound and LiBr (0.26 g, 3 mmol) in acetone (50 ml) was refluxed for 2 hr. The solvent was removed by evaporation, the residue partitioned between $CH_2Cl_2$ (15 ml) and $H_2O$ (10 ml), the organic layer dried ($MgSO_4$), and evaporated to dryness. The impure product was purified on silica using $CH_2Cl_2$ as eluent, to give the bis-bromo ester.

(iv) {3-trifluoromethyl-4-[bis(2-bromoethyl)amino]benzoyl}-L-glutamic acid

The bis-bromo ester was dissolved in TFA (6 ml). After 50 minutes, the solvent was removed by evaporation and the residue washed four times with EtOAc to remove TFA. The oil was re-dissolved in EtOAc, toluene was added and the solvent partly evaporated. The acid crystallized as a pure white solid (45 mg).

Example 9

Figure 1A:
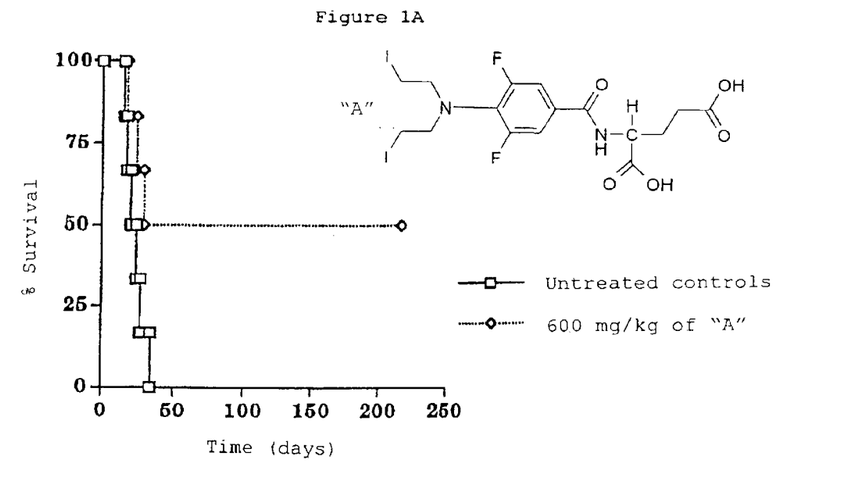
FIG. 1A is a graph of survival rate versus time for Nu/Nu BalbC mice bearing a breast carcinoma xenograft treated with the compound of Example 1, {3,5-difluoro-4-[bis(2-iodoethyl)amino]benzoyl}-L-glutamic acid (denoted "A") at a dosage of 600 mg/kg, as described in Example 9.
Figure 1B:
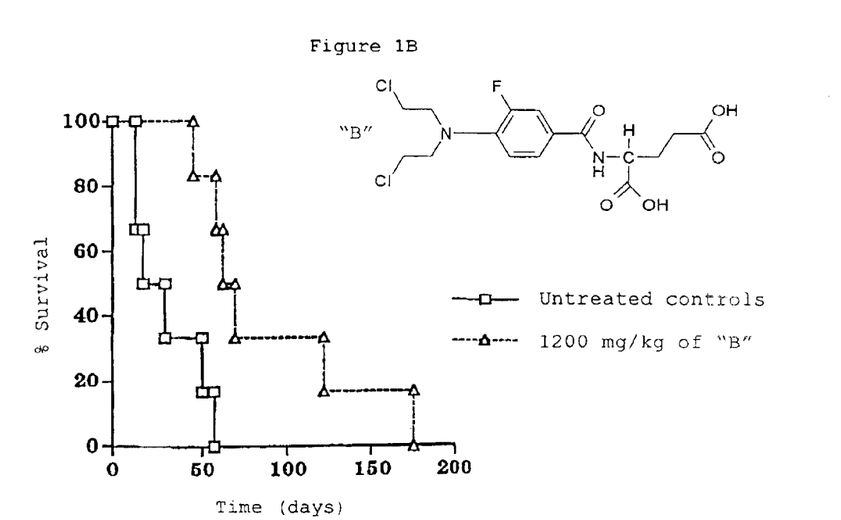
FIG. 1B is a graph of survival rate versus time for Nu/Nu BalbC mice bearing a breast carcinoma xenograft treated with the prior art compound, {3-fluoro-4-[bis(2-chloroethyl)amino]benzoyl}-L-glutamic acid (denoted "B") at a dosage of 1200 mg/kg, as described in Example 9.

The compound of Example 1, (3,5-difluoro-4-[bis(2-iodoethyl)amino]benzoyl)-L-glutamic acid (denoted "A"), was assessed in a Nu/Nu BalbC mouse bearing a breast carcinoma xenograft that comprised 50% cells (MDA MB361) stably expressing β-galactosidase plus 50% cells (MDA MB361) stably expressing a surface tethered carboxypeptidase G2 (CPG2) mutant enzyme (MDA MB361-

STCPG2(O)3) (see WO96/03515). This was compared to the prior art compound, {3-fluoro-4-[bis(2-chloroethyl)amino]benzoyl}-L-glutamic acid (denoted "B"). The controls comprised mice bearing the same tumour xenograft, that were not treated with prodrug.

The results are shown in FIGS. 1A and 1B. As is seen, treatment with 600 mg/kg of the compound of Example 1 ("A", FIG. 1A) provided a 50% survival rate for over 200 days, whereas the untreated control group did not survive for more than 40 days.

With the prior art compound ("B", FIG. 1B) the survival rate of an untreated control group was comparable to the untreated group shown in FIG. 1A, and although treatment provided a measurable effect, and 50% survival was found up to about 70 days post-treatment, it should be noted that to achieve this a higher dose (1200 mg/kg) of the prodrug was required. This translates on a molar basis to 0.98 mM for Example 1 (iv) and 2.9 mM for, the prior art compound.

A number of patents and publications are cited above in order to more fully describe and disclose the invention and the state of the art to which the invention pertains. Each of these references is incorporated herein by reference in its entirety into the present disclosure.

What is claimed is:

1. A compound of Formula I:

(I)

wherein:

$R^1$ is —Cl, —Br, —I, —OSO$_2$CH$_3$, or —OSO$_2$Ph;

$R^2$ is —Cl, —Br, —I, —OSO$_2$CH$_3$, or —OSO$_2$Ph;

wherein Ph denotes a phenyl group which is optionally substituted with 1, 2, 3, 4 or 5 substituents independently selected from a C$_{1-4}$ alkyl group, —F, —Cl, —Br, —I, —CN, or —NO$_2$;

$R^{1a}$ is —H, a C$_{1-4}$alkyl group, or a C$_{1-4}$haloalkyl group;

$R^{2a}$ is —H, a C$_{1-4}$alkyl group, or a C$_{1-4}$haloalkyl group;

$R^{1b}$ is —H, a C$_{1-4}$alkyl group, or a C$_{1-4}$haloalkyl group;

$R^{2b}$ is —H, a C$_{1-4}$alkyl group, or a C$_{1-4}$haloalkyl group;

$R^3$ is —F;

$R^4$ is —F;

$R^5$ is —H;

$R^7$ is —H, —C(CH$_3$)$_3$, or —CH$_2$—CH=CH$_2$;

Z is —CH$_2$-T-W;

T is —CH$_2$—, —O—, —S—, —(S=O)—, or —(SO$_2$)—;

wherein the group —CH$_2$—T—may optionally be substituted with 1 or 2 substituents, denoted Q$^1$ and Q$^2$ respectively, on carbon, wherein Q$^1$ and Q$^2$ are independently a C$_{1-4}$alkyl group or a halogen; or, when Q$^1$ and Q$^2$ are bonded to adjacent carbon atoms, Q$^1$ and Q$^2$ together may form a C$_{3-4}$alkylene radical optionally substituted with 1, 2, 3 or 4 substituents independently selected from C$_{1-4}$alkyl groups and halogens;

W is one of:

(1) —COOH;
(2) —(C=O)OR$^8$;
(3) —(C=O)NR$^9$R$^9$;
(4) —SO$_2$NHR$^{10}$;
(5) —SO$_2$OR$^{11}$;
(6) —PO$_3$R$^{11}$R$^{11}$;
(7) —CONH—SO$_2$R$^{12}$;

with the proviso that if T is —O—, —S—, —(S=O)—, or —(SO$_2$)—, then W is not —COOH;

wherein:

$R^8$ is a C$_{1-6}$alkyl group, a C$_{3-6}$cycloalkyl group, or —CH$_2$—CH=CH$_2$;

$R^9$ is independently —H, a C$_{1-6}$alkyl group, a C$_{3-6}$cycloalkyl group, and wherein the C$_{3-6}$cycloalkyl group may optionally carry a methyl group;

$R^{10}$ is a C$_{1-6}$alkyl group, —CH$_2$—CH=CH$_2$, a C$_{3-6}$cycloalkyl group, or a C$_{1-4}$haloalkyl group;

and wherein the C$_{3-6}$cycloalkyl group may optionally carry a methyl group;

$R^{11}$ represents —H, a C$_{1-6}$alkyl group, or a C$_{3-6}$cycloalkyl group;

$R^{12}$ is one of:

(a) a C$_{3-7}$cycloalkyl group;

(b) a C$_{1-6}$alkyl group, optionally substituted with one or more of: a phenyl group; a phenyl group with from 1 to 5 substituents selected from halogen, —NO$_2$, —CF$_3$, C$_{1-4}$alkyl, C$_{1-4}$alkoxy, —NH$_2$, —NHCOCH$_3$, —CONH$_2$, —OCH$_2$COOH, —NH(C$_{1-4}$alkyl), —N(C$_{1-4}$alkyl)$_2$, —NHCOOC$_{1-4}$alkyl, —OH, —COOH, —CN and —COOC$_{1-4}$alkyl; a C$_{1-4}$alkyl group; a C$_{1-4}$haloalkyl group;

or a halogen; and, (c) a C$_{1-6}$perfluoroalkyl group.

2. A compound according to claim 1, wherein $R^1$ and $R^2$ are independently —I, —Br, or —Cl.

3. A compound according to claim 1, wherein $R^1$ and $R^2$ are both —I.

4. A compound according to claim 1, wherein $R^{1a}$, $R^{1b}$, $R^{2a}$, $R^{2b}$ are each independently —H or —CH$_3$.

5. A compound according to claim 2, wherein $R^{1a}$, $R^{1b}$, $R^{2a}$, $R^{2b}$ are each independently —H or —CH$_3$.

6. A compound according to claim 3, wherein $R^{1a}$, $R^{1b}$, $R^{2a}$, $R^{2b}$ are each independently —H or —CH$_3$.

7. A compound according to claim 1, wherein $R^{1a}$, $R^{1b}$, $R^{2a}$, $R^{2b}$ are all —H.

8. A compound according to claim 2, wherein $R^{1a}$, $R^{1b}$, $R^{2a}$, $R^{2b}$ are all —H.

9. A compound according to claim 3, wherein $R^{1a}$, $R^{1b}$, $R^{2a}$, $R^{2b}$ are all —H.

10. A compound according to claim 1, wherein Z is —CH$_2$-T—C(=O)OH or —CH$_2$—T—C(=O)OR$^8$; and, T is —CH$_2$—.

11. A compound according to claim 2, wherein Z is —CH$_2$—T—C(=O)OH or —CH$_2$—T—C(=O)OR$^8$; and, T is —CH$_2$—.

12. A compound according to claim 3, wherein Z is —CH$_2$—T—C(=O)OH or —CH$_2$—T—C(=O)OR$^8$; and, T is —CH$_2$—.

13. A compound according to claim 4, wherein Z is —CH$_2$—T—C(=O)OH or —CH$_2$—T—C(=O)OR8; and, T is —CH$_2$—.

14. A compound according to claim 5, wherein Z is —CH$_2$—T—C(=O)OH or —CH$_2$—T—C(=O)OR$^8$; and, T is —CH$_2$—.

15. A compound according to claim 6, wherein Z is —CH$_2$—T—C(=O)OH or —CH$_2$—T—C(=O)OR$^8$; and, T is —CH$_2$—.

16. A compound according to claim 7, wherein Z is —CH$_2$—T—C(=O)OH or —CH$_2$—T—C(=O)OR$^8$; and, T is —CH$_2$—.

17. A compound according to claim 8, wherein Z is —CH$_2$—T—C(=O)OH or —CH$_2$—T—C(=O)OR$^8$; and, T is —CH$_2$—.

18. A compound according to claim 9, wherein Z is —CH$_2$—T—C(=O)OH or —CH$_2$—T—C(=O)OR$^8$; and, T is —CH$_2$—.

19. A compound according to claim 1, wherein R$^8$ is —H, —C(CH$_3$)$_3$, or —CH$_2$—CH=CH$_2$.

20. A compound according to claim 2, wherein R$^8$ is —H, —C(CH$_3$)$_3$, or —CH$_2$—CH=CH$_2$.

21. A compound according to claim 3, wherein R$^8$ is —H, —C(CH$_3$)$_3$, or —CH$_2$—CH=CH$_2$.

22. A compound according to claim 4, wherein R$^8$ is —H, —C(CH$_3$)$_3$, or —CH$_2$—CH=CH$_2$.

23. A compound according to claim 5, wherein R$^8$ is —H, —C(CH$_3$)$_3$, or —CH$_2$—CH=CH$_2$.

24. A compound according to claim 6, wherein R$^8$ is —H, —C(CH$_3$)$_3$, or —CH$_2$—CH=CH$_2$.

25. A compound according to claim 7, wherein R$^8$ is —H, —C(CH$_3$)$_3$, or —CH$_2$—CH=CH$_2$.

26. A compound according to claim 8, wherein R$^8$ is —H, —C(CH$_3$)$_3$, or —CH$_2$—CH=CH$_2$.

27. A compound according to claim 9, wherein R$^8$ is —H, —C(CH$_3$)$_3$, or —CH$_2$—CH=CH$_2$.

28. A compound according to claim 10, wherein R$^8$ is —H, —C(CH$_3$)$_3$, or —CH$_2$—CH=CH$_2$.

29. A compound according to claim 11, wherein R$^8$ is —H, —C(CH$_3$)$_3$, or —CH$_2$—CH=CH$_2$.

30. A compound according to claim 12, wherein R$^8$ is —H, —C(CH$_3$)$_3$, or —CH$_2$—CH=CH$_2$.

31. A compound according to claim 13, wherein R$^8$ is —H, —C(CH$_3$)$_3$, or —CH$_2$—CH=CH$_2$.

32. A compound according to claim 14, wherein R$^8$ is —H, —C(CH$_3$)$_3$, or —CH$_2$—CH=CH$_2$.

33. A compound according to claim 16, wherein R$^8$ is —H, —C(CH$_3$)$_3$, or —CH$_2$—CH=CH$_2$.

34. A compound according to claim 16, wherein R$^8$ is —H, —C(CH$_3$)$_3$, or —CH$_2$—CH=CH$_2$.

35. A compound according to claim 17, wherein R$^8$ is —H, —C(CH$_3$)$_3$, or —CH$_2$—CH=CH$_2$.

36. A compound according to claim 18, wherein R$^8$ is —H, —C(CH$_3$)$_3$, or —CH$_2$—CH=CH$_2$.

37. A compound selected from:
{3,5-diiluoro-4-[bis(2-iodoethyl)amino]benzoyl}-L-glutamic acid;
{3,5-difluoro-4-[bis(2-chloroethyl)amino]benzoyl}-L-glutamic acid;
{3,5-difluoro-4-[bis(2-bromoethyl)amino]benzoyl}-L-glutamic acid;
{3,5-difluoro-4-[bis(2-bromopropyl)amino] benzoyl}-L-glutamic acid;
and, the di-tert-butyl esters thereof.

38. A compound selected from:
{3,5-difluoro-4-[bis(2-iodoethyl)amino]benzoyl}-L-glutamic acid;
and, the di-tert-butyl ester thereof.

39. A compound of Formula II:

wherein:
R$^1$ is-Cl, —Br, —I, —OSO$_2$CH$_3$, or —OSO$_2$Ph;
R$^2$ is —C, —Br, —I, —OSO$_2$CH$_3$, or —OSO$_2$Ph;
wherein Ph denotes a phenyl group which is optionally substituted with 1, 2, 3, 4 or 5 substituents independently selected from a C$_{1-4}$ alkyl group, —F, —Cl, —Br, —I, —CN, or —NO$_2$;
R$^{1a}$ is —H, a C$_{1-4}$alkyl group, or a C$_{1-4}$haloalkyl group;
R$^{2a}$ is —H, a C$_{1-4}$alkyl group, or a C$_{1-4}$haloalkyl group;
R$^{1b}$ is —H, a C$_{1-4}$alkyl group, or a C$_{1-4}$haloalkyl group;
R$^{2b}$ is —H, a C$_{1-4}$alkyl group, or a C$_{1-4}$haloalkyl group;
R$^3$ is —F;
R$^4$ is —F; and
R$^5$ is —H.

40. A compound according to claim 39, wherein R$^1$ and R$^2$ are independently —I, —Br, or —Cl.

41. A compound according to claim 39, wherein R$^1$ and R$^2$ are both —I.

42. A compound according to claim 39, wherein R$^{1a}$, R$^{1b}$, R$^{2a}$, R$^{2b}$ are each independently —H or —CH$_3$.

43. A compound according to claim 40, wherein R$^{1a}$, R$^{1b}$, R$^{2a}$, R$^{2b}$ are each independently —H or —CH$_3$.

44. A compound according to claim 41, wherein R$^{1a}$, R$^{1b}$, R$^{2a}$, R$^{2b}$ are each independently —H or —CH$_3$.

45. A compound according to claim 39, wherein R$^{1a}$, R$^{1b}$, R$^{2a}$, R$^{2b}$ are all —H.

46. A compound according to claim 40, wherein R$^{1a}$, R$^{1b}$, R$^{2a}$, R$^{2b}$ are all —H.

47. A compound according to claim 41, wherein R$^{1a}$, R$^{1b}$, R$^{2a}$, R$^{2b}$ are all —H.

48. A compound selected from:
3,5-difluoro-4-[bis(2-iodoethyl)amino]benzoic acid;
3,5-difluoro-4-[bis(2-chloroethyl)amino]benzoic acid;
3,5-difluoro-4-[bis(2-bromoethyl)amino]benzoic acid; and
3,5-difluoro-4-[bis(2-bromopropyl)amino]benzoic acid.

49. 3,5-difluoro-4-[bis(2-iodoethyl)amino]benzoic acid.

50. A composition comprising a compound according to claim 1, and a pharmaceutically acceptable carrier or diluent.

51. A composition comprising a compound according to claim 37, and a pharmaceutically acceptable carrier or diluent.

52. A composition comprising a compound according to claim 38, and a pharmaceutically acceptable carrier or diluent.

* * * * *